128-24 A    AU 335    EX
10/2/79    XR    4,169,984

United States Patent [19]
Parisi

[11] 4,169,984
[45] Oct. 2, 1979

[54] ULTRASONIC PROBE

[75] Inventor: Tulio Parisi, San Diego, Calif.

[73] Assignee: Contract Systems Associates, Inc., San Diego, Calif.

[21] Appl. No.: 746,167

[22] Filed: Nov. 30, 1976

[51] Int. Cl.$^2$ .................. H01L 41/10; A61B 17/32
[52] U.S. Cl. .................... 310/323; 310/325; 32/58; 32/DIG. 4; 128/24 A; 128/305
[58] Field of Search ............ 128/24 A, 303.14, 303.13, 128/2 V, 303 R, 305; 259/DIG. 15, DIG. 44; 318/116, 118; 310/323, 325; 32/58, 53, DIG. 4, DIG. 8; 15/145; 51/59 SS

[56] References Cited
U.S. PATENT DOCUMENTS

| Re. 28,752 | 3/1976 | Balamuth et al. | 128/24 A |
|---|---|---|---|
| 2,130,661 | 9/1938 | Zaebst | 15/145 |
| 3,518,766 | 7/1970 | Burt | 32/58 |
| 3,681,627 | 8/1972 | Murry et al. | 310/325 |
| 3,857,387 | 12/1974 | Shock | 128/24 A |
| 3,990,452 | 11/1976 | Murry et al. | 128/305 |

*Primary Examiner*—Robert W. Michell
*Assistant Examiner*—Arthur S. Rose
*Attorney, Agent, or Firm*—Lowe, King, Price & Becker

[57] ABSTRACT

An ultrasonic, surgical and dental probe comprises a piezoelectric crystal transducer assembly positioned in compression between a pair of body members in a housing. Each body member along with the transducer assembly is mounted on a hollow connecting rod. An interchangeable operative tip, disposed within the hollow connecting rod, is releasably secured to the housing. In a first embodiment, one end of the tip contains a keyhole slot that snap fits to a transverse pin in the housing. In another embodiment, the body of the tip contains a set of threads which engages a corresponding set of threads formed on the inner wall of the connecting rod. Also disclosed is a unique dental descaling tip used in conjunction with the ultrasonic probe. The working end of the tip which contacts the surface of the teeth contains a first orifice. The orifice discharges fluid for irrigation as the working end of the tip cuts into accretions formed on the teeth during ultrasonic vibration. A second orifice, spaced apart from the end of the tip, also discharges fluid for more gently bathing the teeth. Another tip disclosed for removing cataract tissue from the eye contains a single orifice at the working end for irrigating the eye while ultrasonically pulverizing the cataract. During surgery, a small piece of medical grade tubing is inserted into an incision made on the eye. After performing an anterior capsulectomy, the tip is lowered through the tube into contact with the cataract. The tube helps control the position of the tip against the cataract during ultrasonic pulverization, and serves as a drain for cataract particles.

11 Claims, 12 Drawing Figures

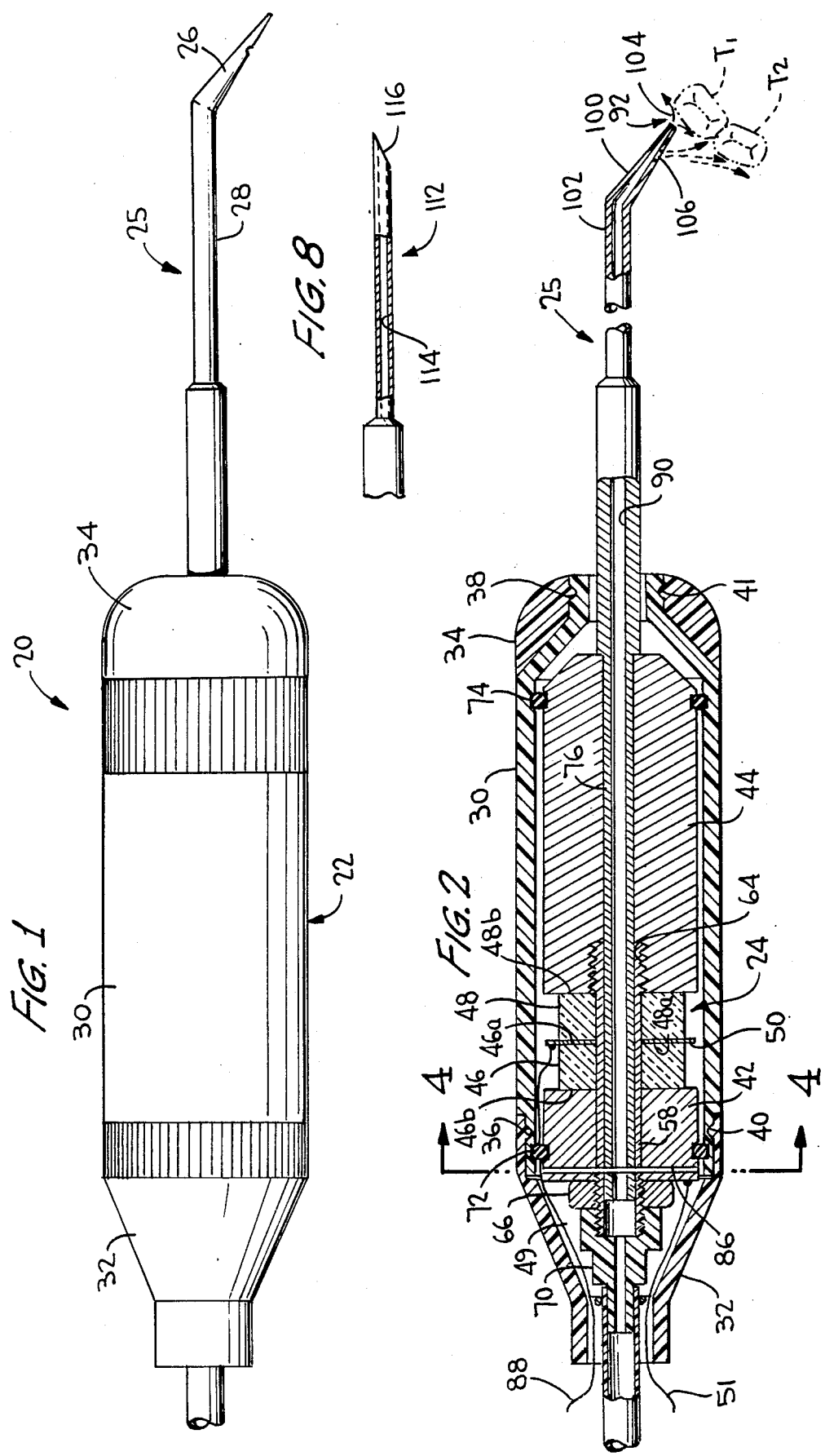

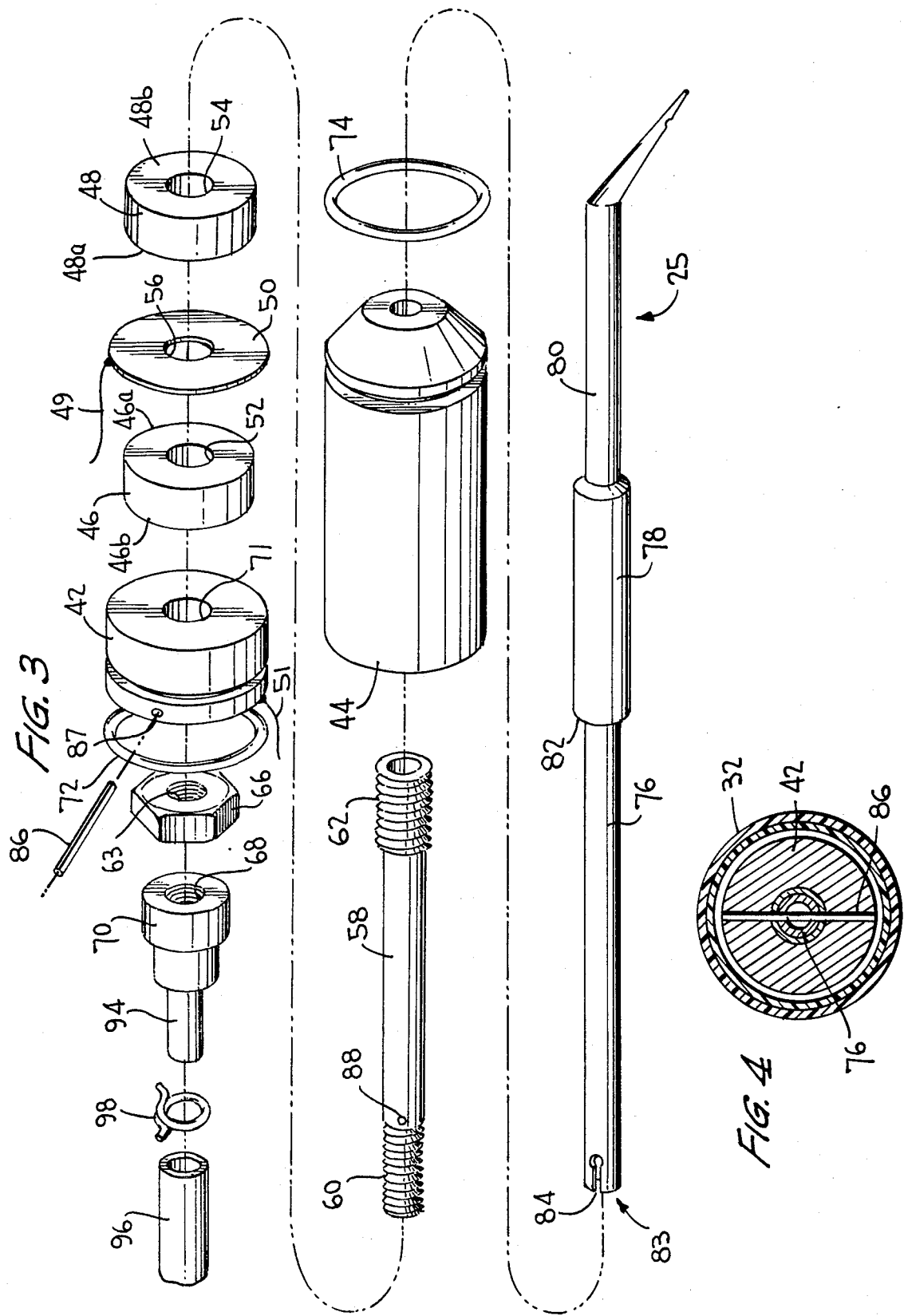

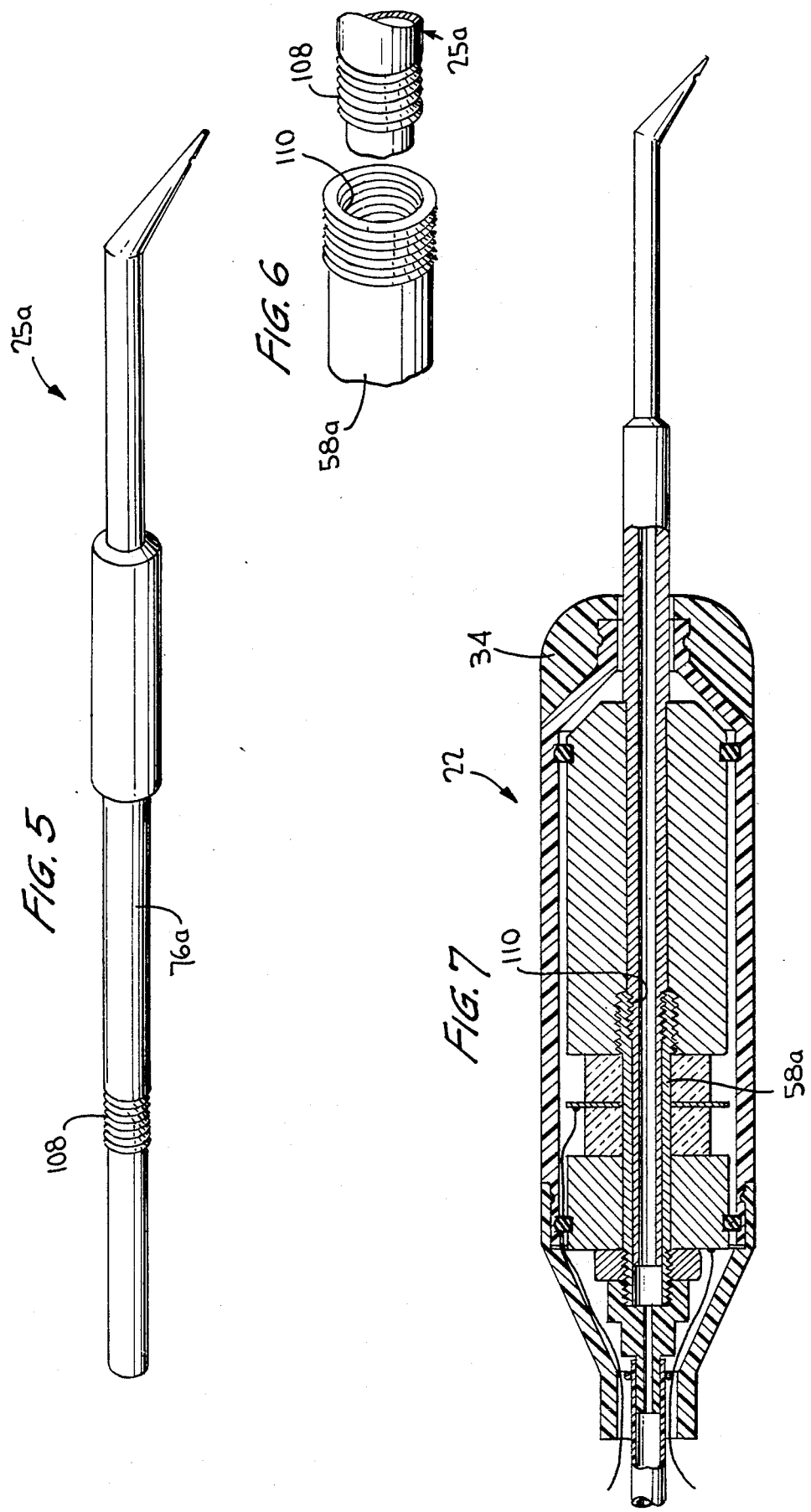

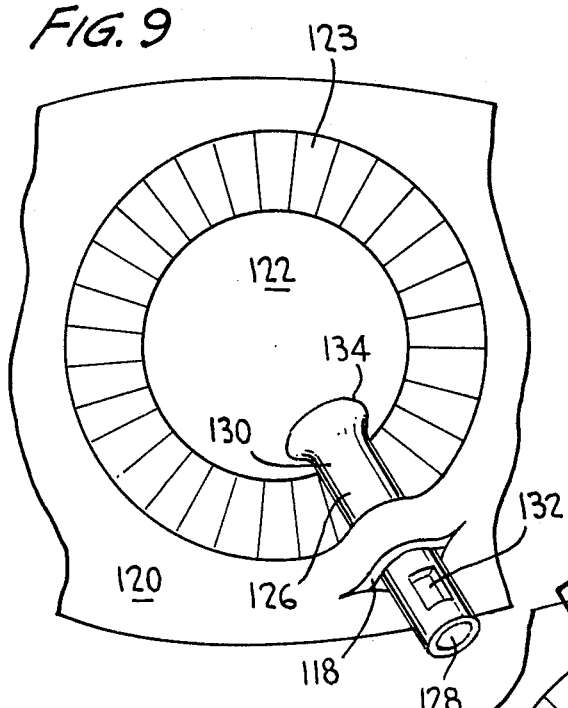
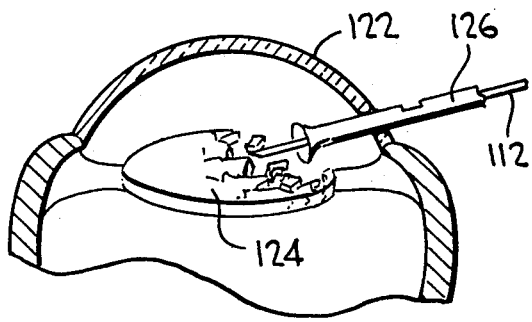
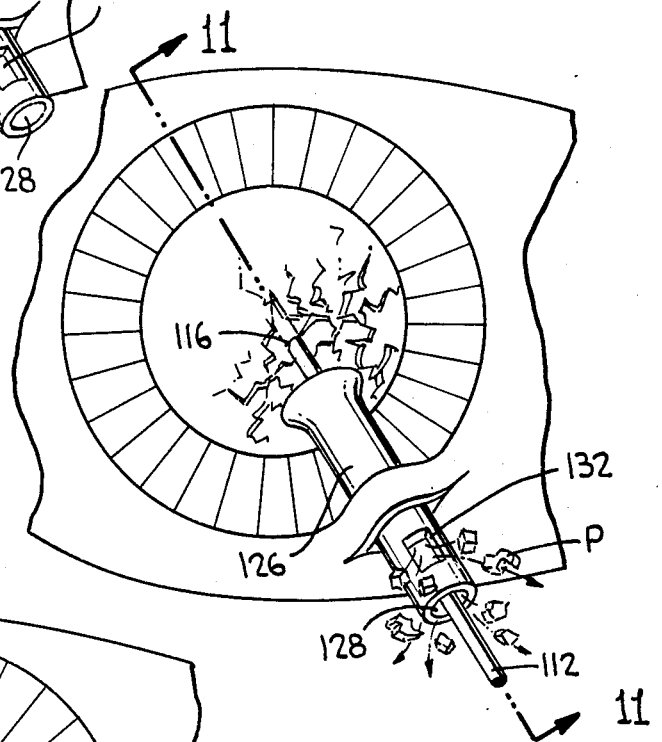
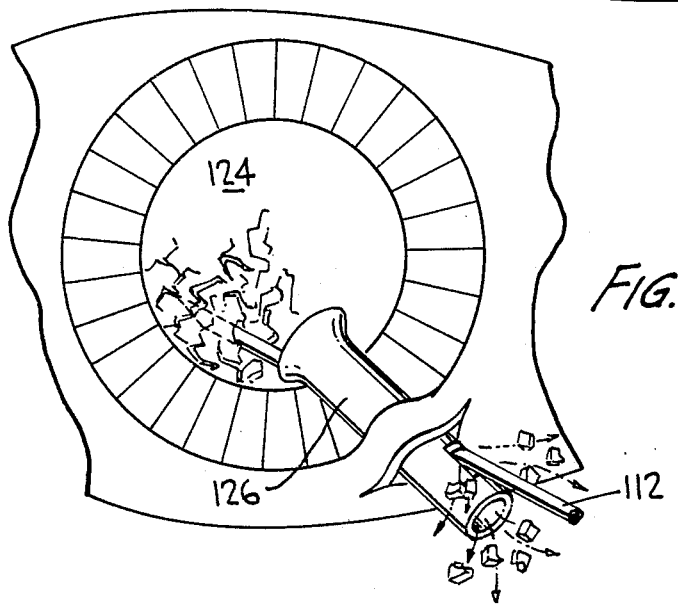

ULTRASONIC PROBE

BACKGROUND OF THE INVENTION

The present invention relates generally to methods of and apparatus for ultrasonically removing material, and more particularly, toward a highly efficient and versatile ultrasonic probe as well as methods of using the probe for descaling the teeth and pulverizing cataract tissue.

Dental and surgical procedures involving the use of an ultrasonic probe for removing tissue are well known. For example, in dentistry, various ultrasonic probes having operative tips that are caused to vibrate at a frequency of about 30,000 Hz with a stroke of about 1 mil are applied to the teeth and vibrated to remove scale and plaque from tooth surfaces. A tip of the probe which is formed of a thin, hollow titanium tube, besides cutting away the scale and plaque during vibration, also serves as an irrigation conduit. A fluid is caused to flow through the tip by gravity to produce a flushing action from the tip as the vibrating tip removes plaque and scale formations. A wide variety of special interchangeable tips are generally provided for removing various types of accretions from the tooth surfaces in different regions of the mouth.

One object of the present invention, therefore, is to provide a new and improved ultrasonic probe for removing dental scale and plaque from tooth surfaces.

In the past, in opthalmological surgery, cataract removal has been commonly undertaken using standard intracapular cataract extraction techniques which, although generally satisfactory, require a prolonged recovery time of up to several months. Recently, a procedure known as phaco-emulsification, or use of an ultrasonic probe to break up and remove cataracts, has become widely used because it offers a remarkable decrease in recovery time; a patient can sometimes return to work the day after surgery. In accordance with this procedure for removal of cataract tissue, as described in the article entitled "History of Emulsification And Aspiration of Senile Cataracts," by Charles D. Kelman, appearing in Transaction of the American Academy of Opthalmology and Otoaryngology, Volume 78, January–February, 1974, pages OP5-13 (originally presented at the 78th Annual Meeting of the American Academy of Ophthalmology and Otoaryngology, Dallas, Tex., Sept. 16-20, 1973), a tip in the form of a hollow tube is inserted into the anterior chamber of the eye through a small incision into contact with the cataract tissue. The tip is vibrated by a hand held probe at an ultrasonic rate, and hydrodynamic flow of a special solution is established in order to prevent collapse of the anterior chamber. As particles of the cataract tissue are cut from the cataract mass, the particles are removed from the chamber through the tip of the ultrasonic probe. In the case of hard cataracts, these particles, which have a tendency to slide into contact with the walls of the chamber, have an abrasive character. Certain portions of the eye are more prone to abrasion sensitivity. Accordingly, the cataract particles must be completely drained from the anterior chamber without contacting the chamber walls.

During aspiration of cataract tissue, the tip of the ultrasonic probe must be very carefully manipulated under the field of view of a microscope in order to prevent aspirating other than cataract tissue. Close control of the tip is especially critical at the peripheral regions of the cataract.

Accordingly, one object of the invention is to provide a new and improved probe for ultrasonically removing tissue.

Another object of the invention is to provide a new and improved ultrasonic probe for performing phaco-emulsification for cataract removal.

Still another object of the invention is to provide a new and improved probe and method for performing cataract removal using phaco-emulsification wherein cataract particles are completely drained from the anterior chamber to avoid damage to delicate eye tissue, and an operative tip is precisely controlled in the peripheral as well as central regions of the cataract.

In prior art devices of which I am aware, substantial energy loss in caused by poor coupling between the piezoelectric crystals and operative tip of the hand held probe. The reason for poor coupling is that the crystals are positioned within a housing so as to extend along only a small portion of the operative tip of the probe, and the vibrational energy applied to the tip has difficulty overcoming the mass of the tip body.

The housing of the probe is typically of unitary construction. Occasionally, the probe must be serviced to correct electrical or mechanical breakdowns. It is difficult to gain access into the housing, and once in, the individual elements of the probe, e.g., piezoelectric crystals, cannot be readily disassembled.

Furthermore, several different tips are generally used during a surgical procedure, such as dental descaling or phaco-emulsification. These tips must be quickly interchanged during each procedure. Binding up of the tips within the housing frequently occurs in ultrasonic probes of the type described, and this slows down the surgical procedure.

Accordingly, an additional object of the invention is to provide a new and improved ultrasonic probe having improved energy transfer efficiency to the operative tip.

Another object of the invention is to provide a new and improved ultrasonic probe that is easy to dissemble and service, as needed.

Still another object of the invention is to provide a new and improved ultrasonic probe, wherein the operative tips thereof are readily interchangeable.

BRIEF DESCRIPTION OF THE INVENTION

An ultrasonic probe for removing tissue from a human being or other animal, particularly for removing scale and plaque from the surfaces of teeth or removing cataract tissue from the eye, comprises a housing containing a piezoelectric crystal transducer prestressed by a pair of body members. Interchangeable tips, each of which is formed of a thin, titanium tube, are releasably secured to the housing. The unique structure of the probe provides efficient transfer of ultrasonic energy between the piezoelectric transducer and tips, and permits quick and easy changeover.

The piezoelectric crystal assembly comprises first and second disc-shaped piezoelectric crystals, each having a central bore. The crystals are mounted in-line to each other on a hollow connecting rod within the housing. The ends of the connecting rod are threaded to engage with sets of threads formed in the first body member and in an adjusting nut. With the crystals seated between the body members, the spacing between the members is adjusted by the nut to prestress the crystals for maximum power output.

One end of the tip extends into the housing through the hollow connecting rod. The crystals extend along a substantial portion of the connecting rod so that there is highly efficient energy transfer between the crystals and tip through the rod.

Quick release means is provided on the tip for easy changeover. In one embodiment, the quick release means comprises a transverse pin within the housing that releasably engages a key hole slot formed in the end of the tip. The tip is inserted into the housing and rotated until the slot and pin are aligned with each other. Then the tip is snapped onto the pin. In another embodiment, a portion of the inner wall of the hollow connecting rod is threaded to engage with a set of external threads formed on the body of the tip. The tip is inserted down into the housing into abutment with the connecting rod, and then twisted to lock.

The housing is formed of a molded material, such as plastic, and comprises a central, cylindrical member, and a pair of end members. The end members press fit onto the central members for easy disassembly.

A high frequency alternating voltage for energizing the piezoelectric crystals is applied across the crystals by a first wafer electrode located between the crystals. A second electrode is applied to the body members in contact with opposite faces of the crystal. The body members, along with the connecting rod, are electrically conductive so that the alternating voltage is applied across the entire length of both crystals. Since the opposite ends of the crystals are energized in phase to each other relative to the abutting crystal faces, vibratory forces coupled to the connecting rod end and tip are maximized. The body members and crystals are insulated from the housing by a pair of insulators, such as O-rings.

A tip for descaling teeth, in accordance with the invention, used in conjunction with the inventive ultrasonic device, comprises a thin, hollow titanium tube having a body portion and a short end portion that form an obtuse angle with respect to one another. The working end of the tip contains a first orifice through which fluid is sprayed as that end is maintained against the surface of the teeth for descaling and plaque removal. The egress of fluid from the first orifice helps remove accretions from the surface of the teeth and provides irrigation. A second orifice, spaced apart from the working end of the tip, provides a second egress of fluid for bathing the surface of the teeth with a broader, less intense fluid spray.

Another tip for pulverizing cataract tissue from the eye comprises a thin, titanium tube having a tapered working end. In removing a cataract, an incision is first formed on the eye, and an anterior capsulectomy is performed to gain access to the cataract. A medical grade tube of small diameter is seated into the incision. Then, the working end of the tip is extended through the tube into contact with the cataract. The tip is vibrated at an ultrasonic rate to pulverize the cataract, and the pulverized cataract tissue is expelled from the eye through the tube.

The tube contains an inlet end, an outlet end and an opening formed in the tube wall. The central portion of the cataract is pulverized by positioning the tip through the inlet and outlet ends of the tube so that the tip is oriented along the axis of the tube. The peripheral portions of the cataract are pulverized by positioning the tip through the wall opening and outlet end of the tube so that the tip is oblique to the tube axis.

Besides serving as a guide to the tip for more precise positioning of the tip against the cataract tissue during surgery, the tube also functions as a drainage conduit for cataract particles to ensure complete removal of the particles from the anterior chamber of the eye.

Still other objects and advantages of the present invention will become readily apparent to those skilled in this art from the following detailed description, wherein I have shown and described only the preferred embodiments of the invention, simply by way of illustration of the best modes contemplated by me of carrying out my invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

FIG. 1 is a side view of an ultrasonic probe utilizing a unique dental descaling tip, in accordance with one aspect of the invention;

FIG. 2 is a cross sectional side view of one embodiment of the probe showing the operation of the dental descaling tip against the teeth surfaces;

FIG. 3 is an exploded view of the probe shown in FIG. 2 exposing a keyhole slot formed in one end of the tip and a cooperating transverse pin;

FIG. 4 is a cross sectional end view of the probe taken along the line 4—4 in FIG. 2 showing the transverse pin in more detail;

FIG. 5 is a perspective view of a dental tip in accordance with a second aspect of the invention;

FIG. 6 is a detailed view of the tip shown in FIG. 5 in cooperation with a connecting rod in accordance with a second embodiment of the invention;

FIG. 7 is a cross sectional side view of a probe utilizing the tip shown in FIG. 5;

FIG. 8 is a partial view of a tip used in conjunction with a probe for phaco-emulsification;

FIG. 9 is a top view of an eye showing a medical grade tube extending into the anterior chamber through an incision made on the eye, in accordance with an improved phaco-emulsification procedure;

FIG. 10 is an illustration of the tip shown in FIG. 9 in contact with a central portion of the cataract, cataract particles being expelled from the anterior chamber through the tube;

FIG. 11 is a cross sectional view of a cataract pulverization taken along the line 11—11 in FIG. 10; and FIG. 12 is an illustration of a tip in contact with a peripheral portion of the cataract through a medical grade tube, with cataract particles being expelled from the anterior chamber of the eye through the tube.

DETAILED DESCRIPTION OF THE PREFERRED EMBODIMENTS

Referring to FIGS. 1–4, and initially to FIGS. 1 and 2, an ultrasonic probe 20, used for ultrasonically removing tissue or other material, comprises a handle or housing 22 containing a piezoelectric transducer assembly 24 for imparting ultrasonic vibrations to an operative tip 25 formed preferably of titanium. As shall be described in more detail below, the tip 25 extends through a central aperture or bore in piezoelectric transducer 24, and because the transducer extends along a substantial portion of the tip, there is highly efficient energy transfer between the transducer and the tip.

The housing 22, formed preferably of molded plastic, includes a cylindrical, central member 30 and end members 32, 34. Annular recesses 36 and 38 are formed in central member 30 (FIG. 2) and end members 32,34 contain annular ribs 40,41, respectively. The ribs 40,41 fit into the annular recesses 36,38. The end members 32,34 are retained to center member 30 by these corresponding annular ribs and recesses when the end members are press-fitted to the central member, as shown in FIG. 2.

Referring to FIGS. 2 and 3, transducer assembly 24 comprises a first piezoelectric crystal 46 and a second piezoelectric crystal 48 located within housing 22 on opposite sides of a disc-shaped electrode 50. The crystals 46, 48 and electrode 50 are seated in housing 22 between body members 42,44 formed of an electrically conductive material, such as aluminum. Body members 42,44, as well as crystals 46,48 and electrode 50, are maintained in axial alignment to each other by connecting rod 58 which passes through bores 52,54 of crystals 46,48 as well as through aperture 56 of electrode 50.

Rod 58 is a hollow tube also formed of electrically conductive material, such as aluminum, and has threaded ends 60,62. End 60 of rod 58 is coupled to a threaded bore 68 of collar 70, and end 62 of the rod 58 is coupled to threaded bore 64 within body member 44. A nut 66 is also threaded onto end 60 of connecting rod 58 in abutment to body member 42 and collar 70 for maintaining body member 42 against crystal 46. Bore 71 of body member 42 is unthreaded.

Piezoelectric transducer assembly 24 is prestressed within housing 22 by compression between body members 42,44. The body members 42,44 are urged against transducer assembly 24 by first tightening nut 66 on threaded end 60 of connecting rod 58 until the assembly 24 is compressed so as to generate a maximum ultrasonic vibration output. This can be done by monitoring the vibration output of tip 25 as nut 66 is tightened, but in practice, the nut is tightened by an amount determined by experience to provide substantial ultrasonic vibrational output from crystal assembly 24. Nut 66 is then locked in place by collar 70.

The body members 42 and 44 are electrically and mechanically insulated from housing 22 by O-rings 72 and 74. The O-rings 72 and 74 float the body members 42,44 within the housing 22, so that during ultrasonic vibration of the tip 25, vibration is not coupled to the housing 22 thereby permitting more precise control of the tip by a dentist or surgeon.

The tip 25 is an elongated, hollow titanium tube having a base portion 76, an enlarged portion 78 and a working portion 80. A shoulder 82 interfaces the base portion 76 and enlarged portion 78 (FIG. 3). The end 83 of base portion 76 contains a keyhole slot 84 for snap fitting to a corresponding transverse pin 86 in housing 22.

Referring to FIG. 3, the tip 25 is inserted into housing 22 through first body member 42 and connecting rod 58. Pin 86 is seated within first body member 42 and connecting rod 58 through radial apertures 86 and 87. The base portion 76 of tip 25 snap fits to pin 86 by rotating the tip 25 until there is alignment between keyhole slot 84 and pin 86, and then snapping the tip onto the pin. Shoulder 82 of tip 25 is maintained in abutment with body member 44 as shown in FIG. 2.

Still referring to FIG. 2, a high frequency source (not shown) of alternating voltage is supplied to transducer assembly 24 through opening 88 in end member 32 of housing 22. Wire 49 from one terminal of the source is connected to electrode 50 and wire 51 from the opposite terminal of the source is connected to body member 42. Abutting faces 46a,48a of crystals 46,48 at electrode 50 thus receive one polarity of the source of high frequency alternating voltage, and opposite faces 46b,48b of crystals 46,48 receive an opposite polarity voltage. Body members 42,44, along with connecting rod 58, provide an alternating potential difference between the opposite faces 46b,48b of crystals 46,48 and the faces 46a,48a abutting electrode 50.

With an alternating voltage of an ultrasonic frequency applied between body members 42,44 and electrode 50, e.g., 30 KHz voltage piezoelectric crystals 46,48 vibrate in a known manner at an ultrasonic frequency. The magnitude of the ultrasonic vibration is substantial, e.g., 1 mil, because the crystals 46,48 are maintained in compression between body members 42,44 and furthermore, because the energizing voltage is applied completely across the bodies of the crystals.

Ultrasonic vibration from crystals 46,48 are mechanically coupled to connecting rod 58, and the vibrations in turn are mechanically coupled from the connecting rod to the base portion 76 of tip 25. Coupling between the crystals 46,48 and tip 25 is highly efficient because the vibrations are imparted directly to the connecting rod 58 which extends along a substantial length of the base portion 76 of tip 25. Therefore, the entire subassembly composed of crystals 46,48 and connecting rod 58 imparts vibrations to the tip 25. This is in contrast to prior art devices of which I am aware wherein ultrasonic vibrations are imparted directly to a tip by a piezoelectric transducer assembly. In addition, since opposite faces 46b and 48b of crystals 46 and 48 are energized in phase to each other relative to the faces 46a,48a, the magnitude of the vibrational energy coupled to the connecting rod 58 is thereby maximized.

Tip 25 also contains a longitudinal channel 90 (FIG. 2) for transferring an irrigating fluid from an external fluid source (not shown) to the working end of the tip. The fluid is supplied to tail 94 of collar 70 through a fluid-carrying conduit 96 (FIG. 3). The conduit 96 is secured to collar 94 with a ring clamp 98. In general, the fluid is gravity fed to tip 25 by a fluid receptacle (not shown) that is elevated above tip 25 to establish a continuous fluid flow. The fluid is typically tap water for dental irrigation purposes.

Referring to FIG. 2, tip 25, in accordance with one aspect of the invention, is a dental descaling tip having a distal portion 100 and a remaining portion 102. The distal portion 100 and remaining portion 102 form an obtuse angle with respect to one another. The distal portion 100 tapers to a working end 92, and contains a first orifice 104 at the working end, and a second orifice 106. The second orifice 106 is located on the distal portion 100 spaced apart from the working end 104.

During descaling, the tip 25 is ultrasonically vibrated by transducer assembly 24 as fluid flow is established through channel 90 of the tip 25 toward the working end 92. Fluid egresses from the first orifice 104, irrigating the surfaces of the teeth as the fluid cuts through accretions formed on the teeth surfaces. The fluid from first orifice 104 flushes away particles cut from the teeth and cuts through plaque formed between the gum and teeth. Meanwhile, egress of fluid from the second orifice 106 bathes the teeth with a broader, less intense spray, as shown. The combination of fluid egressing from the first orifice 104 and the less intense spray of fluid from orifice 106 both agitates the surface of the teeth cutting away scale and plaque, and bathes the teeth. In FIG. 2, as particles are removed from tooth T1 at orifice 104, loose particles that drain onto tooth T2 are washed away by the spray of fluid from orifice 106.

As aforementioned, in accordance with the embodiment of FIGS. 2–4, tip 25 is releasably secured to housing 22 by keyhole slot 84 in the tip that snap fits to transverse pin 86. In accordance with another embodiment of the invention, referring now to FIGS. 5–7, a tip 25a is similar to tip 25, but a set of threads 108 is formed on base portion 76a of the tip in place of keyhole slot 84. A corresponding set of threads 110 is formed on the inner wall of connecting rod 58a (FIG. 7) and tip 25a extends into the connecting rod with sets of threads 108 and 110 interfitting each other, as shown in FIG. 6.

In order to connect tip 25a to housing 22, the dentist or surgeon simply inserts the tip into the mouth of end member 34 until the set of threads 108 on the tip 25a contact threads 110 in connecting rod 58. Then the dentist or surgeon twists the tip until the threads 108 lock within threads 110.

Referring now to FIG. 8, another tip 112 is used for emulsification of cataracts in a phaco-emulsification procedure. Tip 112, preferably formed of titanium, contains a channel 114 for guiding a flow of fluid into the eye during emulsification. The working end 116 of the tip 112 is tapered, as shown. The diameter of the tip is less than 1 mm.

Referring to FIGS. 9–12, a unique procedure for removing cataract tissue from an eye using probe 20, in accordance with the invention, is disclosed. Referring to FIG. 9, a 3 mm incision 118 is formed on the eye 120 at anterior chamber 122. The pupil 123 of the eye is dilated, and an anterior capsulectomy is performed to gain access to cataract 124 (see FIG. 11). A short length of 3 mm diameter medical grade tubing 126 is inserted into anterior chamber 122 through incision 118. The tube 126 has an inlet 128, an outlet 130, and a sidewall opening 132. A portion of the tube 126 at outlet 130 is flanged as shown as 134. The tube 126 is formed of a suitable medical grade material such as Silastic, manufactured by Dow Corning Corporation.

Referring to FIGS. 10 and 11, tip 112 is guided through tube 126 into the anterior chamber 122 of eye 120 into contact with cataract 124. The tip 112 is in contact with a central portion of cataract 124, as shown, and is positioned along the longitudinal axis of the tube 126 by locating the tip between inlet 128 and outlet 130 of the tube. Tip 112 is vibrated at an ultrasonic frequency as a suitable fluid such as a saline solution egresses from the working end 116. As the working end 116 of tip 112 pulverizes cataract tissue, the fluid egressing from end 116 tends to maintain the anterior chamber 122 in equilibrium. That is, the amount of fluid entering chamber 122 of eye 120 through end 116 of tip 112 compensates for the amount of fluid being discharged from the chamber 112 preventing deflation of the chamber.

Cataract particles and fluid (FIG. 10) are discharged from anterior chamber 122 through inlet 128 and sidewall aperture 132 of tube 126. The tube 130 thus functions (1) as a drain tube for guiding fluid discharge from the eye, whereby abrasive cataract particles are prevented from irritating eye tissues, and (2) as a guide for steadying tip 112 against the cataract mass 124.

Referring to FIG. 12, the tube 126 also guides tip 112 into contact with the peripheral regions of the cataract 124. This is done by the surgeon as he locates tip 112 through sidewall aperture 132 and outlet 130 of the tube into contact with the cataract 124. By working the tip 112 in the position shown in FIGS. 10 and 11, the entire extent of cataract 124 can be accessed by tip 112 and control of the tip is precise throughout all regions of the cataract 124.

In this disclosure, there is shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. Ultrasonic probe, comprising:
   a housing;
   piezoelectric transducer means located in said housing, said transducer means containing an axial bore;
   an elongated operative tip extending through said axial bore of said transducer means and having a shoulder formed thereon at a longitudinal position spaced from said transducer means;
   first and second body members arranged in axial alignment within said housing on opposite sides of said transducer means;
   said first and second body members having respective axial bores in alignment with the axial bore of said transducer means;
   a connecting rod extending through said axial bores of said second body member and said transducer means and extending partially through said axial bore of said first body member and interconnecting said body members;
   means for adjusting the spacing between said first and second body members to prestress said transducer means by compressing said transducer means between said body members;
   electrode means for applying an alternating electric voltage across said transducer means; and
   securing means for releasably securing said tip to at least said first body member and said transducer means with said shoulder in abutment with said first body member;
   said first body member being elongated and providing contact with said tip over a substantial portion of the length of said bore of said first body member.

2. The apparatus of claim 1 wherein said operative tip is further releasably secured to said second body member.

3. The apparatus of claim 1, wherein said connecting rod is hollow to receive said tip.

4. The apparatus of claim 1, wherein said securing means includes an anchor member located in said housing, and an end of said tip in said housing includes attachment means for snap fitting said tip to said anchor member.

5. The apparatus of claim 4, wherein said anchor member comprises a transverse pin seated in one of said body members, and said tip contains a keyhole slot for snap fitting to said pin.

6. The apparatus of claim 1, wherein said securing means includes thread means for threadably securing said tip to said connecting rod, wherein an inner wall of said connecting rod contains a first set of threads, and a body portion of said tip contains a second set of threads, said tip being positioned within said rod with said first and second sets of threads in engagement with each other.

7. The apparatus of claim 1, wherein said transducer means includes first and second piezoelectric transducers axially aligned to each other on said connecting rod.

8. The apparatus of claim 7, wherein said first and second transducers are annular and have oppositely directed faces, said electrode means includes first electrode means positioned between said first and second transducers, and second electrode means positioned on said opposite annular faces of said first and second transducers.

9. The apparatus of claim 8, wherein said first and second body members and said connecting rod are electrically conductive, said second electrode means being formed by said body members and said connecting rod, an alternating voltage being applied across said first electrode means and one of said first and second body members, said electrically conductive connecting rod supplying said voltage to the other one of said body members.

10. The apparatus of claim 9, including insulating means for insulating said first and second body members from said housing.

11. The apparatus of claim 10, wherein said insulating means includes an O-ring located on an outer surface of each of said body members.

* * * * *